United States Patent
Lee (10) Patent No.: US 7,678,106 B2
(45) Date of Patent: Mar. 16, 2010

(54) GYNECOLOGICAL ABLATION PROCEDURE AND SYSTEM

(75) Inventor: Bruce B. Lee, Carmel, CA (US)

(73) Assignee: Halt Medical, Inc., Pleasanton, CA (US)

( * ) Notice: Subject to any disclaimer, the term of this patent is extended or adjusted under 35 U.S.C. 154(b) by 1364 days.

(21) Appl. No.: 11/033,351

(22) Filed: Jan. 10, 2005

(65) Prior Publication Data

US 2005/0149013 A1    Jul. 7, 2005

Related U.S. Application Data

(63) Continuation-in-part of application No. 09/920,425, filed on Jul. 31, 2001, now Pat. No. 6,840,935.

(60) Provisional application No. 60/224,191, filed on Aug. 9, 2000.

(51) Int. Cl.
*A61B 18/04* (2006.01)
*A61B 18/18* (2006.01)

(52) U.S. Cl. .......................... 606/34; 606/41

(58) Field of Classification Search .......... 606/41, 606/31–50; 607/101–102
See application file for complete search history.

(56) References Cited

U.S. PATENT DOCUMENTS

| | | | |
|---|---|---|---|
| 35,330 | A | 5/1862 | Silvester |
| 3,991,770 | A | 11/1976 | LeVeen |
| 4,016,886 | A | 4/1977 | Doss et al. |
| 4,074,718 | A | 2/1978 | Morrison, Jr. |
| 4,080,959 | A | 3/1978 | Leveen |
| 4,095,602 | A | 6/1978 | Leveen |
| 4,119,102 | A | 10/1978 | Leveen |
| 4,140,130 | A | 2/1979 | Storm, III |
| 4,154,246 | A | 5/1979 | Leveen |
| 4,230,129 | A | 10/1980 | Leveen |
| 4,285,346 | A | 8/1981 | Armitage |
| 4,290,435 | A | 9/1981 | Waggott |
| 4,303,636 | A | 12/1981 | Gordon |
| 4,346,715 | A | 8/1982 | Gammell |
| 4,375,220 | A | 3/1983 | Matvias |
| 4,545,368 | A | 10/1985 | Rand et al. |
| 4,565,200 | A | 1/1986 | Cosman |
| 4,676,258 | A | 6/1987 | Inokuchi et al. |
| 4,709,701 | A | 12/1987 | Weber |

(Continued)

OTHER PUBLICATIONS

Bergamini, MD, et al., *Laparoscopic radiofrequency thermal ablation: A new approach to symptomatic uterine myomas*, American Journal of Obstetrics and Gynecology (2005) 192, 768-73, Varese, Italy.

*Primary Examiner*—Michael Peffley
(74) *Attorney, Agent, or Firm*—Thompson Hine LLP; Anthony H. Handal (57) ABSTRACT

A method for treating tumors, such as uterine leiomyomata, includes inserting an ablation apparatus into a pelvic region and positioning the ablation apparatus into a pelvic tumor. The method further includes using a laparoscope and an imaging device, such as an ultrasound machine, to confirm the location of the pelvic tumor and placement of the ablation apparatus. The method further includes delivering electromagnetic energy or other energy through the ablation apparatus to the pelvic tumor to directly ablate the tumor. A surgical system for ablating pelvic tumors is also provided.

37 Claims, 4 Drawing Sheets

U.S. PATENT DOCUMENTS

| | | | |
|---|---|---|---|
| 4,773,864 A | 9/1988 | Holt |
| 4,823,791 A | 4/1989 | D'Amelio et al. |
| 4,881,543 A | 11/1989 | Trembly et al. |
| 4,887,614 A | 12/1989 | Shirakami et al. |
| 4,955,884 A | 9/1990 | Grossi et al. |
| 4,962,761 A | 10/1990 | Golden |
| 5,003,991 A | 4/1991 | Takayama et al. |
| 5,007,908 A | 4/1991 | Rydell |
| 5,010,897 A | 4/1991 | Leveen |
| 5,099,756 A | 3/1992 | Franconi et al. |
| 5,151,101 A | 9/1992 | Grossi et al. |
| 5,190,517 A | 3/1993 | Zieve et al. |
| 5,190,541 A | 3/1993 | Abele et al. |
| 5,234,004 A | 8/1993 | Hascoet et al. |
| 5,257,451 A | 11/1993 | Edwards et al. |
| 5,273,535 A | 12/1993 | Edwards et al. |
| 5,275,162 A | 1/1994 | Edwards et al. |
| 5,282,797 A | 2/1994 | Chess |
| 5,293,863 A | 3/1994 | Zhu et al. |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,322,503 A | 6/1994 | Desai |
| 5,328,467 A | 7/1994 | Edwards et al. |
| 5,334,193 A | 8/1994 | Nardella |
| 5,342,357 A | 8/1994 | Nardella |
| 5,348,554 A | 9/1994 | Imran et al. |
| 5,363,861 A | 11/1994 | Edwards et al. |
| 5,366,490 A | 11/1994 | Edwards et al. |
| 5,368,592 A | 11/1994 | Stern et al. |
| 5,370,678 A | 12/1994 | Edwards et al. |
| 5,383,917 A | 1/1995 | Desai et al. |
| 5,385,544 A | 1/1995 | Edwards et al. |
| 5,398,683 A | 3/1995 | Edwards et al. |
| 5,403,311 A | 4/1995 | Abele et al. |
| 5,409,453 A | 4/1995 | Lundquist et al. |
| 5,423,807 A | 6/1995 | Milder |
| 5,423,808 A | 6/1995 | Edwards et al. |
| 5,423,811 A | 6/1995 | Imran et al. |
| 5,433,708 A | 7/1995 | Nichols et al. |
| 5,435,805 A | 7/1995 | Edwards et al. |
| 5,437,662 A | 8/1995 | Nardella |
| 5,456,662 A | 10/1995 | Edwards et al. |
| 5,458,596 A | 10/1995 | Lax et al. |
| 5,458,597 A | 10/1995 | Edwards et al. |
| 5,462,521 A | 10/1995 | Brucker et al. |
| 5,470,308 A | 11/1995 | Edwards et al. |
| 5,470,309 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,531,677 A | 7/1996 | Lundquist et al. |
| 5,536,267 A | 7/1996 | Edwards et al. |
| 5,540,655 A | 7/1996 | Edwards et al. |
| 5,542,915 A | 8/1996 | Edwards et al. |
| 5,542,916 A | 8/1996 | Hirsch et al. |
| 5,542,928 A | 8/1996 | Evans et al. |
| 5,545,161 A | 8/1996 | Imran |
| 5,545,171 A | 8/1996 | Sharkey et al. |
| 5,545,193 A | 8/1996 | Fleischman et al. |
| 5,546,267 A | 8/1996 | Frederiksen et al. |
| 5,549,108 A | 8/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,560,358 A | 10/1996 | Arnold et al. |
| 5,562,703 A | 10/1996 | Desai |
| 5,582,610 A | 12/1996 | Grossi et al. |
| 5,662,680 A | 9/1997 | Desai |
| 5,672,173 A | 9/1997 | Gough et al. |
| 5,672,174 A | 9/1997 | Gough et al. |
| 5,683,384 A | 11/1997 | Gough et al. |
| 5,728,143 A | 3/1998 | Gough et al. |
| 5,759,162 A | 6/1998 | Oppelt et al. |
| 5,782,827 A | 7/1998 | Gough et al. |
| 5,810,764 A * | 9/1998 | Eggers et al. ............... 604/23 |
| 5,911,036 A | 6/1999 | Wright et al. |
| 5,935,123 A | 8/1999 | Edwards et al. |
| 5,979,453 A * | 11/1999 | Savage et al. ............. 128/898 |
| 6,002,968 A | 12/1999 | Edwards |
| 6,036,689 A | 3/2000 | Tu et al. |
| 6,066,139 A | 5/2000 | Ryan et al. |
| 6,071,280 A | 6/2000 | Edwards et al. |
| 6,190,383 B1 | 2/2001 | Schmaltz et al. |
| 6,212,433 B1 | 4/2001 | Behl |
| 6,217,518 B1 | 4/2001 | Holdaway et al. |
| 6,254,601 B1 | 7/2001 | Burbank et al. |
| 6,355,033 B1 | 3/2002 | Moorman et al. |
| 6,575,969 B1 | 6/2003 | Rittman et al. |
| 6,837,887 B2 | 1/2005 | Woloszko et al. |
| 6,840,935 B2 | 1/2005 | Lee |
| 2003/0125729 A1 | 7/2003 | Hooven et al. |
| 2003/0130711 A1 | 7/2003 | Pearson et al. |
| 2003/0199868 A1 | 10/2003 | Desai et al. |
| 2004/0215182 A1 | 10/2004 | Lee |
| 2004/0254572 A1 | 12/2004 | McIntyre et al. |
| 2005/0149013 A1 | 7/2005 | Lee |
| 2006/0189972 A1 | 8/2006 | Grossman |

* cited by examiner

GYNECOLOGICAL ABLATION PROCEDURE AND SYSTEM

RELATED APPLICATIONS

This application is a continuation-in-part of U.S. patent application Ser. No. 09/920,425, filed Jul. 31, 2001, now U.S. Pat. No. 6,840,935, which claims priority to U.S. Provisional Patent Application No. 60/224,191, filed Aug. 9, 2000. This application is related to U.S. patent application Ser. No. 10/853,599, filed May 24, 2004. These prior patent applications are incorporated by reference herein for all purposes.

BACKGROUND OF THE INVENTION

1. Field of Invention

The present invention relates to a procedure and system for treating gynecological disorders. More particularly, the present invention relates to the treatment of abdomino-pelvic tumors.

2. Discussion of the Related Art

Benign and malignant tumors can occur in the abdomen and pelvis. For example, uterine leiomyomata are muscle cell tumors that occur in 77% of women in the reproductive years. Although uterine leiomyomata rarely (0.1%) progress to cancer, these tumors can cause excessive menstrual bleeding, irregular bleeding, pregnancy loss, infertility, urinary frequency and retention, increased abdominal girth, and pelvic and/or abdominal pressure or pain with sexual activity, menses, or daily activities. Women with uterine leiomyomata frequently incur surgical procedures (e.g., hysterectomy, dilatation and curettage, myomectomy, endometrial ablation, and hysteroscopy), medical and hormonal therapies, office visits, and a variety of radiologic procedures (e.g., ultrasounds, CAT scans, and MRIs), in an effort to treat these tumors. Uterine leiomyomata account for approximately 200,000 hysterectomies per year in the United States alone, at a direct cost of well over $2 billion. Hysterectomies carry a morbidity rate of 1%, with 2,000 deaths per year and 240,000 complications per year in North America.

Uterine leiomyomata are most often multiple, and may be subserosal (i.e., bulging externally from the uterus), intramural (i.e., growing within the wall of the uterus), submucosal (i.e., extending partially into or completely contained within the uterine cavity), or pedunculated (i.e., growing externally with a stalk-like base). Because patients may have multiple uterine leiomyomata at different locations, current conservative surgeries may involve both an abdominal and a vaginal (hysteroscopic) approach, thereby necessitating two procedures.

Investigators have utilized a laser or bipolar cautery to perform myolysis or destruction of these tumors, although neither of these methods is performed in significant numbers today. These methods necessarily destroy normal overlying and surrounding tissue in order to treat the tumor. As a result, the integrity of the uterus is compromised, and harmful scar tissue (e.g., adhesions) may occur. Previous methods have also treated only those tumors visible on the external uterine surface. Thus, there is a need for an improved method of treating benign and malignant pelvic tumors that does not damage the overlying tissue. Such an improved method could be used on women who wish to later conceive and subsequently deliver. There is also a need for a single method capable of treating all sizes of subserosal, intramural, submucuosal, and pedunculated tumors in all locations. A single method, which would relieve most or all symptoms of abdominal or pelvic pain/pressure, increased abdominal girth, abnormal uterine bleeding, urinary frequency and retention, infertility, and miscarriage, is also needed. In addition, it would be desirable for the method and system to better preserve the uterus while being less invasive, less costly, safer, more cosmetic, and with a faster and less painful recovery than conventional methods of treating pelvic tumors.

SUMMARY

The present invention, also referred to as "the Halt procedure," is an innovative, outpatient procedure that utilizes electromagnetic energy to effectively ablate pelvic tumors. The invention employs an ablation device that uses radio-frequency (RF) energy to treat pelvic tumors, while sparing the surrounding normal tissue. Although the ablation device utilized in the present invention has FDA approval for ablation of soft tissue tumors, no known reports exist in the medical literature of the ablation device's application to uterine leiomyomata or other pelvic tumors. In addition, current results indicate that, compared to other conservative therapies, the present method is very effective. Thus far, the present invention has provided relief from most types of symptoms caused by uterine leiomyomata. Furthermore, the present invention is versatile, safe, and well-accepted by patients. Advantages of the present invention include a quick recovery time, typically no more than a week, and significant cost savings. More importantly, the present invention provides a practical and efficient way to achieve uterine conservation on an out-patient basis.

In accordance with one embodiment of the present invention, a method of treating a tumor includes inserting an ablation device into a pelvic region, the ablation device including an electrode; positioning the electrode within a tumor; delivering a first amount of energy through the electrode to preheat the tumor; exposing a larger area of the electrode within the tumor; and delivering a second amount of energy through the electrode to directly ablate the tumor.

In accordance with another embodiment of the present invention, a method of treating pelvic tumors includes inserting an ablation device into a pelvic region, the ablation device including an electrode; positioning the electrode within a pelvic tumor with an imaging probe separate from the ablation device; and delivering energy through the electrode to directly ablate the pelvic tumor.

In accordance with yet another embodiment of the present invention, a surgical system for ablating pelvic tumors includes an ablation device including an electrode for insertion into a pelvic tumor; an imaging probe separate from the ablation device for positioning the electrode within the pelvic tumor; and an energy source coupled to the ablation device for providing energy to the electrode to directly ablate the pelvic tumor.

The present invention procedure may be performed by laparoscopy (i.e., placement of a scope usually near the umbilicus), trans-abdominally with or without laparoscopic guidance, transvaginally, or hysteroscopically. The Halt procedure has most often utilized conventional laparoscopy with the additional placement of (1) a supra-pubic port or sleeve (10 mm) at the top of the uterus for insertion of an intra-abdominal ultrasound probe and (2) an ablation device, also usually in the lower abdominal region proximate to the tumors to be treated. The Halt procedure has also been performed by a trans-abdominal technique, utilizing conventional trans-abdominal ultrasound and placement of the ablation device trans-abdominally with laparoscopic confirmation, as well as by a trans-vaginal and a trans-cervical technique.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF DRAWINGS

Use of the same reference symbols in different figures indicates similar or identical items. It is further noted that the drawings may not be drawn to scale.

DETAILED DESCRIPTION

Figure 1:
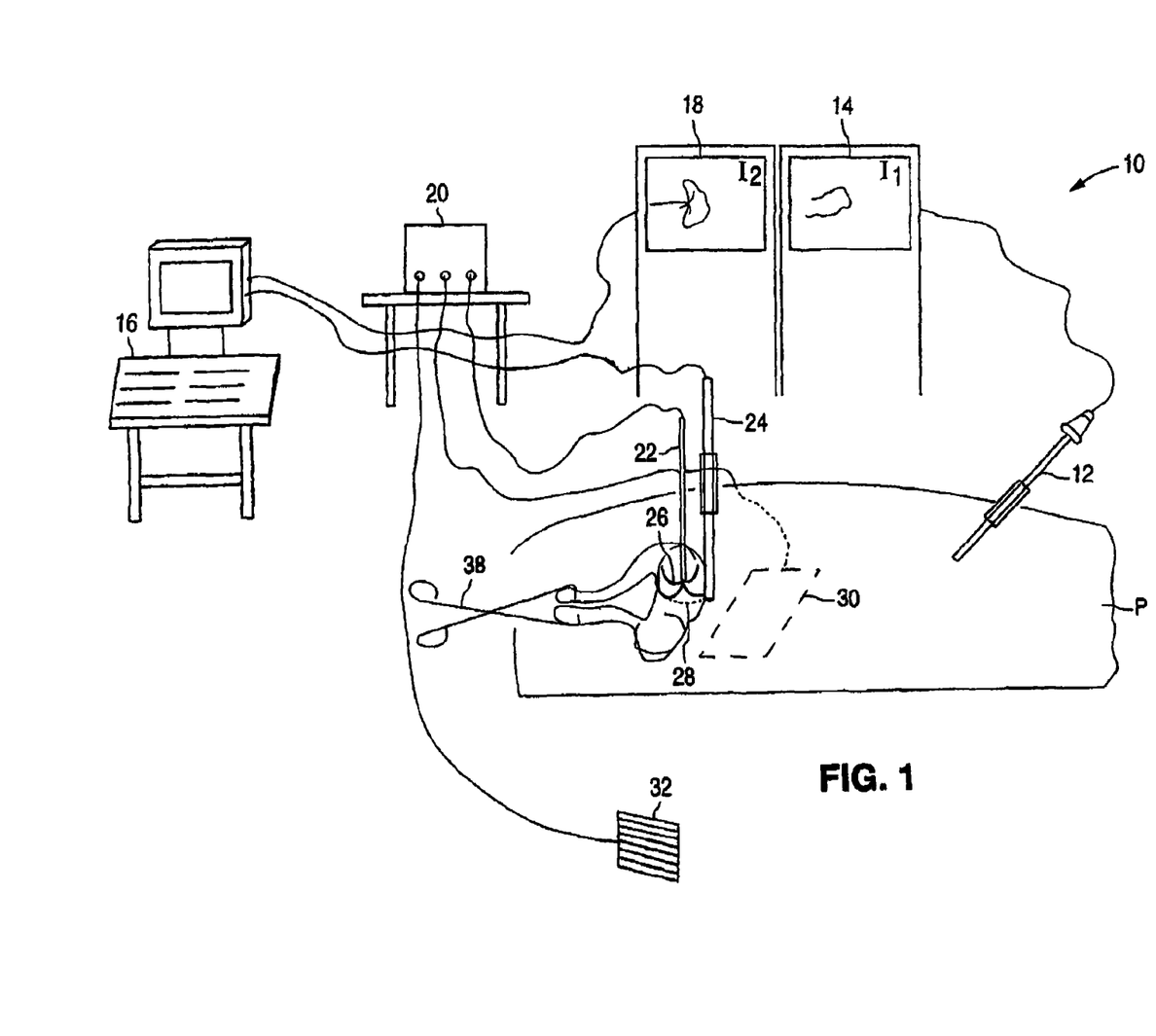
FIG. 1 is a perspective diagram of a surgical system for ablating pelvic tumors in accordance with an embodiment of the present invention.

Referring first to FIG. 1, a surgical system 10 for ablating pelvic tumors includes a laparoscope 12, a video monitor 14 associated with laparoscope 12, an imaging device 16, a video monitor 18 associated with imaging device 16, an energy source 20, and an ablation device 22.

Laparoscope 12, which is inserted into a patient P, is connected to a light source and to a video monitor 14 for displaying an image from laparoscope 12. As will be explained in greater detail below, laparoscope 12 enables a surgeon to view the structures in the pelvis and abdomen and the insertion and placement of ablation device 22 into a pelvic or abdominal region of the patient. Standard recording devices such as a VCR, DVD, or CD recorders may be utilized to record and document laparoscopic images.

Imaging device 16 is connected to a video monitor 18 to provide images of the patient's pelvic region in one example. These images, which are displayed on video monitor 18, enable the surgeon to determine the presence and location of pelvic tumors in one example. In one embodiment, imaging device 16 shown in FIG. 1 includes an imaging probe 24, and in one example is an ultrasound machine including an intra-abdominal ultrasound probe. Recording devices such as a standard VCR, DVD, or CD recorders may be placed at various sites along the signal pathway for documentation and storage purposes. Instead of an intra-abdominal ultrasound probe, a transducer (not shown) may be coupled to the ultrasound machine for trans-abdominal ultrasound imaging. In addition, other imaging devices, such as an MRI machine or a CT device in conjunction with any appropriate imaging probe, may also be used instead of an ultrasound machine.

Ablation device 22 is a sterile, electrosurgical device that includes at least one electrode and may include a plurality of retractable electrodes or arms 26. FIG. 1 shows arms 26 of ablation device 22 deployed in a pelvic tumor 28. Each arm 26 of ablation device 22 is a retractable curved electrode for delivering energy and has a thermocouple (not shown) located at the distal end. In one embodiment, a Doppler transducer may also be incorporated at the distal end of an electrode. Although FIG. 1 shows ablation device 22 as including deployable arms, an ablation device without any arms may also be used. Alternatively, the ablation device or devices may include two or more needles that may be inserted into the tumor. Although the use of one ablation device is described herein, the use of a plurality of ablation devices is within the scope of the present invention.

Examples of applicable ablation devices include, but are not limited to, the Model 30 Electrosurgical Device and the RITA® StarBurst™ XL, both available from RITA Medical Systems, Inc. of Mountain View, Calif., the Cool-tip™ RF Ablation System electrode or cluster electrode from Valleylab of Boulder, Colo., the LeVeen Needle Electrode from Radio-Therapeutics Corporation of Sunnyvale, Calif., and the R.F.$^{gel}$ electrode and the OPAL/OPALflex device from Prosurg Inc. of San Jose, Calif.

Ablation device 22 is coupled to energy source 20, which supplies energy to each of the arms 26 of ablation device 22. Energy source 20 may be an RF generator in one example, including a standard radiofrequency generator commonly used in surgical procedures for cutting and coagulation. The supply of RF energy from energy source 20 to ablation device 22 and to a dispersive electrode 30 is controlled by an operator control, such as by a foot pedal 32. The application of RF energy causes an increase in tumor temperature. At sufficiently high temperatures, e.g., 65 degrees Celsius and above, cell death occurs, thereby destroying the tumor.

Examples of applicable energy sources include, but are not limited to, the Model 500 Generator or the RITA® Model 1500 RF Generator, both available from RITA Medical Systems, Inc. of Mountain View, Calif., and the RF 3000 generator from RadioTherapeutics Corporation of Sunnyvale, Calif.

Energy source 20 may further include a mono-polar or bipolar energy source, which allows the ablation device 22 to utilize traditional mono-polar or bipolar cautery to treat very small, superficial tumors and to ablate the track formed during insertion of ablation device 22. Cauterizing the ablation device track reduces or prevents bleeding upon insertion or withdrawal of ablation device 22 from the organ.

Figure 2:
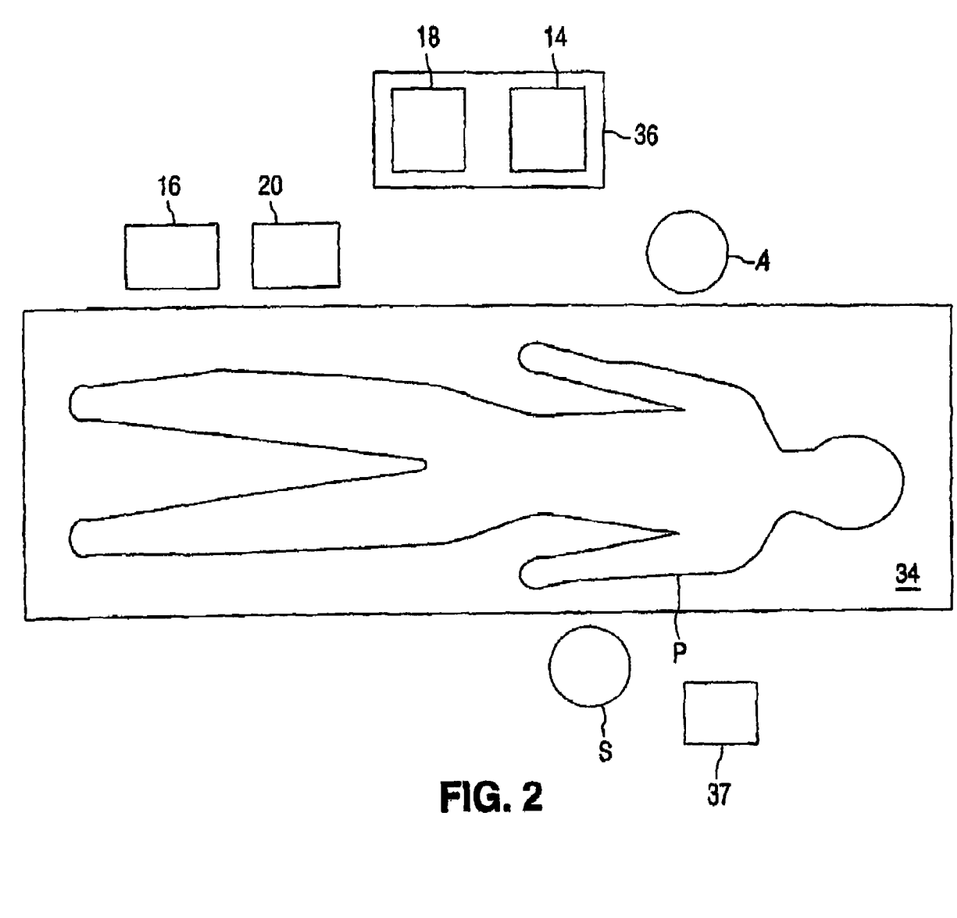
FIG. 2 is a top plan view of the surgical system of FIG. 1, illustrating an arrangement of certain equipment with respect to a patient lying on an operating table.

As better illustrated in FIG. 2, in accordance with an embodiment of the present invention, the equipment of surgical system 10 is set up about the patient in a non-traditional arrangement. FIG. 2 illustrates the patient P lying in a dorsal position on an operating table 34.

A tower 36, which supports video monitor 14 for laparoscope 12 and video monitor 18 for imaging device 16, is located proximate the patient's waist, rather than at the foot of operating table 34. Since the surgeon S is located on the other side of operating table 34 across from tower 36, the surgeon S has a direct view of the monitors 14 and 18. Video monitors 14 and 18 need not be provided on tower 36; they may be suspended from the ceiling and located on the other side of operating table 34 across from the surgeon S. Advantageously, during longer surgical procedures, the placement of video monitors 14 and 18 directly across from the surgeon is more comfortable for the surgeon and safer for the patient, as the surgeon need not turn his/her head toward the foot of operating table 34 to view monitors 14 and 18.

Although FIGS. 1 and 2 show separate video monitors 14 and 18 for laparoscope 12 and imaging device 16, respectively, a single monitor capable of simultaneously displaying multiple images from the laparoscope and the imaging device, such as a picture-in-picture monitor, may also be used. The single monitor would be located across the table from the surgeon S and may be mounted on a tower similar to tower 36, suspended from the ceiling, or otherwise located across the patient from the surgeon for easy viewing by the surgeon.

Tower 36 may include additional equipment (not shown), such as an insufflation machine, a printer, a light source, and a VCR. Tower 36 may be provided with wheels so that it may be easily moved about the operating room.

An additional monitor 37 for laparoscope 12 may also be provided across from a surgical assistant A, who is seated or standing across the table from the surgeon S, at approximately the patient's chest level. Thus, additional monitor 37 would be located adjacent the surgeon S. Additional monitor 37 may be mounted on a movable tower (not shown), suspended from the ceiling, or otherwise appropriately located across from assistant A.

Imaging device 16, which is not located on tower 36, is positioned along operating table 34, across from the surgeon S, and toward the foot of operating table 34. For example, imaging device 16 may be located proximate the patient's knees.

Figure 3:
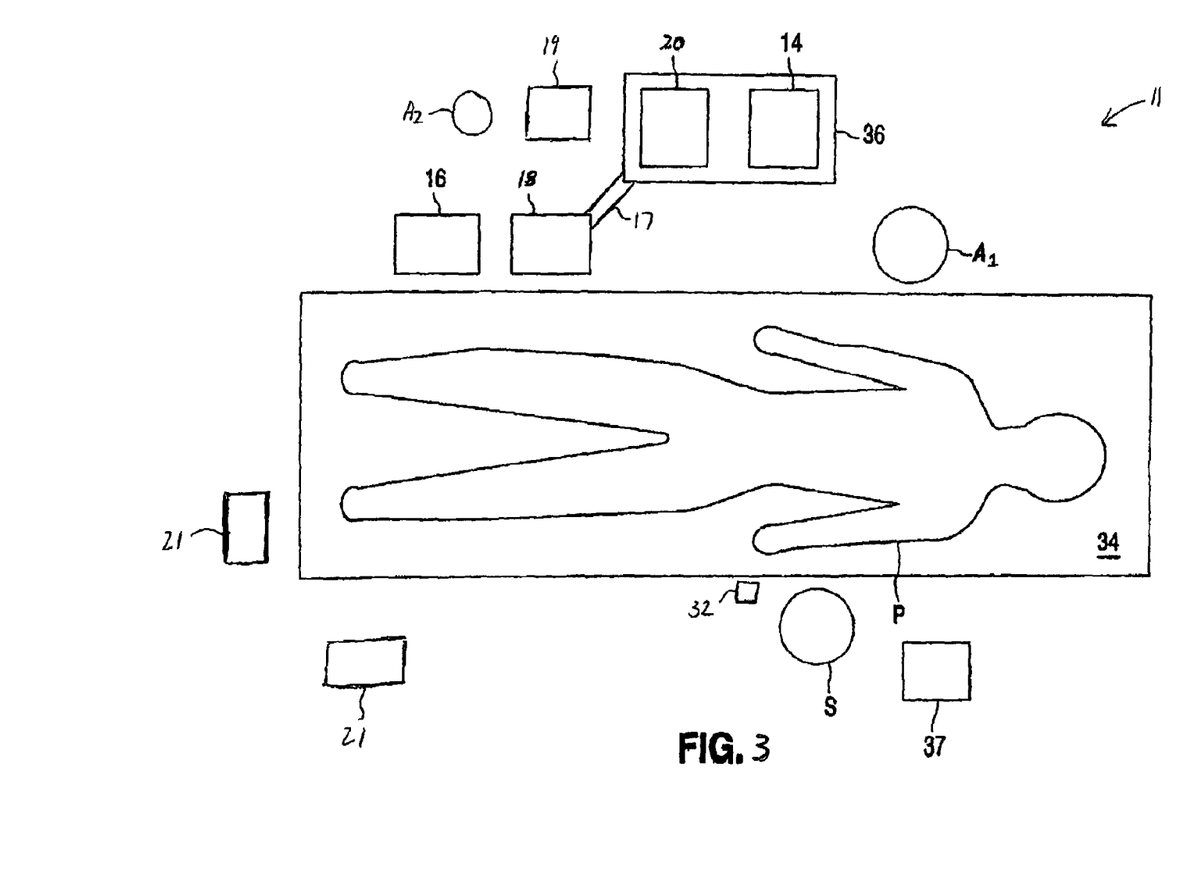
FIG. 3 is a top plan view of a surgical system for ablating pelvic tumors in accordance with another embodiment of the present invention.

Referring now to FIG. 3, a top plan view of a surgical system 11 for ablating pelvic tumors is shown in accordance with another embodiment of the present invention. Equipment similar to that shown in system 10 of FIG. 2 is used and the same reference symbols indicate the same or similar items as in FIG. 2. However, in FIG. 3, energy source 20 is provided on tower 36 and video monitor 18 for the imaging device is provided on a movable platform attached by an arm 17 to tower 36.

As shown in FIG. 3, tower 36, which includes video monitor 14, energy source 20, an insufflation machine (not shown), a printer (not shown), a light source (now shown), and a VCR or digital recording device(s)(not shown), is placed proximate the patient's waist and across from the surgeon S. Video monitor 18 is placed on a moveable platform so that the surgeon S has an unobstructed view of the monitors without having to significantly turn the head. A surgical assistant $A_1$ is located across the table from the surgeon S at about the patient's chest level, with tower 36 located behind the assistant $A_1$ and further toward the foot of operating table 34.

A computer 19, operably coupled to energy source 20, is located next to tower 36 toward the foot of operating table 34. Computer 19 records data from the ablation procedure, including but not limited to temperature, power, impedance, and length of time of ablation. Software for recording the data is available from RITA Medical Systems, Inc. An assistant $A_2$ may be proximate computer 19 to operate energy source 20 and/or computer 19. Imaging device 16 is situated alongside operating table 34 on the same side as the assistant $A_1$ and toward the foot of operating table 34. The additional monitor 37 is positioned across from the surgical assistant $A_1$ at about the patient's chest level. A table 21 for operative instruments may be located along the foot of operating table 34 as shown.

Figure 4:
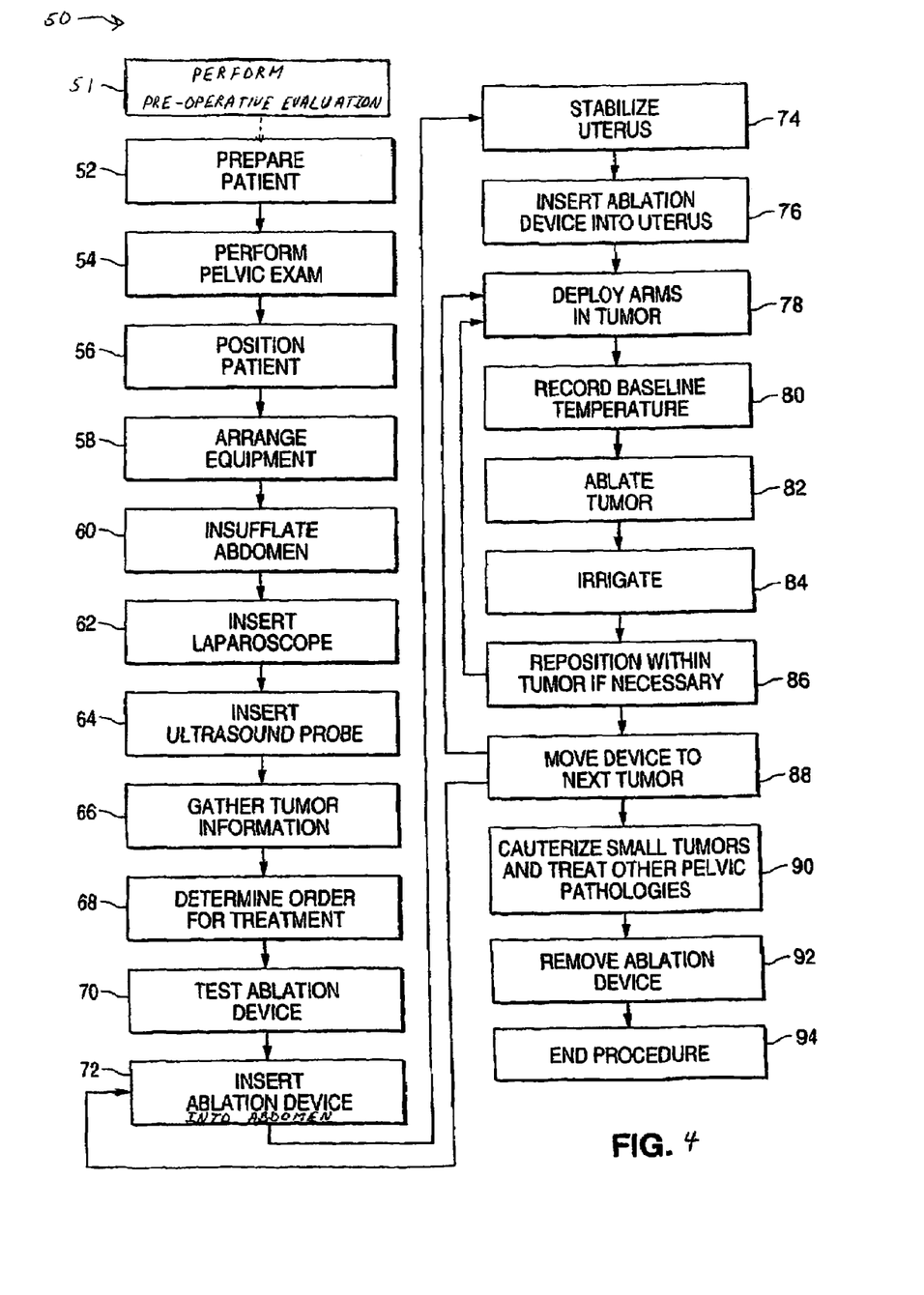
FIG. 4 is a flowchart illustrating a method of ablating pelvic tumors in accordance with an embodiment of the present invention.

A method of treating pelvic tumors, in accordance with one embodiment of the present invention, will now be described, with reference to the flow chart illustrated in FIG. 4. This method 50 employs a laparoscopic technique for ablating pelvic tumors.

At step 51, a pre-operative evaluation is optionally performed prior to the surgery. In one embodiment, the pre-operative study may include physical examination of the uterus, ultrasound examination trans-abdominally and intra-vaginally, and/or Doppler imaging to analyze and to localize blood flow within the myometrium and the tumors themselves. Three-dimensional ultrasound mapping of the patient's pelvic area may also be used to image and map multiple tumors.

After the pre-operative study, the surgical procedure outlined below in conjunction with FIGS. 1-3 may include steps 52 through 94 although not necessarily all the steps. First, at step 52, the patient is prepared for laparoscopy by placing and properly adhering dispersive electrode 30 to the patient's thighs and/or lower back to allow current from the ablation device to be dissipated.

At step 54, the patient is placed under general anesthesia and then positioned for examination of the patient's pelvic region by the surgeon. Such an examination allows the surgeon to confirm the location of palpable tumors and portions of the analysis from the pre-operative study in step 51. A manipulator 38 (FIG. 1), such as a tenaculum, is placed on the patient's cervix, in one embodiment pinching the anterior and posterior lips of the cervix together so as to use the tenaculum as a uterine manipulator. Advantageously, manipulator 38 is not placed inside the uterus thereby reducing the likelihood of infection and/or complications from interaction with other instruments or energy sources. A 14 Fr. Foley catheter is inserted into the patient's bladder for emptying the bladder during the surgical procedure.

At step 56, the patient is placed in a dorsal position with her arms at her sides, rather than extended out as an airplane, and a blanket and a surgical drape are placed over the patient. This position provides the surgeon and surgical assistant with more room to move about. The dorsal position is also a safer position for the patient than a frog-leg or lithotomy position, as the dorsal position reduces the instance of nerve injuries and provides better circulation. In addition, the dorsal position does not require the use of custom drapes and stirrups. The surgical drape contains pouches for at least one laparoscopic cord. Serial compression devices (not shown) are placed on the patient's legs and activated to improve circulation throughout the surgical procedure and reduce the possibility of thrombosis. In addition, the patient may be placed in a bear hugger system (not shown) to assist in the maintenance of the patient's body temperature while under general anesthesia.

At step 58, in one embodiment of the present invention, the equipment is advantageously arranged about operating table 34. FIGS. 2 and 3 illustrate two embodiments of a surgical system for ablating pelvic tumors which system is described above with respect to FIGS. 2 and 3.

At step 60, the surgeon S then makes an infra-umbilical or sub-umbilical or other abdominal incision for safe and advantageous placement of a Verres needle and laparoscopic trocar and sleeve. The Verres needle is then inserted through the incision and into the peritoneal cavity in the standard technique of laparoscopy. The insufflation machine is then used to insufflate the abdomen with carbon dioxide gas until the abdominal pressure is approximately 14-20 mm Hg, thereby providing the surgeon with a window for visualization.

Next, at step 62, a 3, 5, 7, or 10 mm trocar and sleeve are inserted through the infra-umbilical or sub-umbilical incision. The trocar is then removed and laparoscope 12 is inserted into the sleeve. Laparosope 12 and monitor 14 are then used to verify correct placement of laparoscope 12 within the peritoneal cavity and the absence of any trauma. The sleeve is attached to the carbon dioxide gas supply and includes a valve for controlling the abdominal pressure of the peritoneal cavity.

Steps 60 and 62 discussed above describe a closed laparoscopy procedure. For those patients, for whom the surgeon feels an open laparoscopy would be advantageous, the surgeon would make an infra- or sub-umbilical incision and use a combination of blunt and sharp dissection through subcutaneous tissue. The surgeon would then utilize retractors for exposure. When the fascia is visualized, it is grasped with one or more clamps, elevated, and incised. This provides a view of the peritoneum below, which may be bluntly or sharply incised. An appropriate laparoscopic sleeve is then placed, and the abdomen is insufflated with carbon dioxide gas. The laparoscope is then inserted into the peritoneal cavity through the sleeve.

At step 64, the surgeon then uses laparoscope 12, while palpating a top of the uterine fundus, to determine an optimal location for an intra-abdominal ultrasound probe. The optimal location is generally at the most cephalad extent of the uterus in the midline, rather than supra-pubic or lateral. This usually provides the best vantage point from which to visualize all surfaces of the uterus. Other locations may be utilized if deemed appropriate by the operating surgeon.

An incision is then made at this location and a 3, 5, 7, or 10 mm trocar and sleeve are inserted. The trocar is removed and imaging probe 24 is inserted into the sleeve. By way of example, the imaging probe 24 may be an Aloka model no. UST-5526L-7.5 MHz probe for use with an Aloka model no. SSD 1400 ultrasound machine. Imaging probe 24 transmits a signal to imaging device 16 which then displays an image of the pelvic region on video monitor 18 based upon the signal. Thus, the surgeon may simultaneously view the images on video monitors 14 and 18. As discussed above, a single monitor that simultaneously displays images from laparoscope 12 and imaging device 16 may be used instead of separate monitors 14 and 18.

At step 66, the surgeon examines the entire pelvis and abdomen to confirm the presence or absence of any visible pathological conditions. The surgeon also uses laparoscope 12 and imaging probe 24 to visualize any tumors, such as uterine leiomyomata. In particular, the surgeon takes note of the number, location, and size of all tumors, and compares that information with previously acquired data from the pre-operative evaluation in step 51 and the pelvic examination in step 54. Advantageously, imaging probe 24 allows for uterine manipulation and imaging in real-time.

At step 68, the surgeon formulates and/or modifies the existing ablation plan and determines an order for treating the tumors. This order is determined based on the sizes and locations of the various tumors, and whether or not the tumors are accessible from a single point of insertion of the ablation device or if multiple locations are required. For example, if two tumors are generally along the same track of ablation device 22, the surgeon may first ablate the deeper tumor and, upon retraction of ablation device 22, ablate the remaining tumor. In addition, in larger tumors requiring multiple overlapping ablations, the surgeon may choose to ablate first a portion of the tumor that is furthest away from the vasculature of that tumor and work toward the vasculature, or vice versa.

At step 70, the surgeon tests ablation device 22 to ensure that it is operating properly. Ablation device 22 is connected to energy source 20, and proper feedback from the thermocouples, if any, is observed. In particular, the surgeon operates foot pedal 32, or any other appropriate operator control, to activate the supply of RF energy from energy source 20 and notes an appropriate rise in temperature and any peaks. The ablation device 22 may also be flushed with saline prior to use to keep the electrode cool and to reduce char formation.

At step 72, the surgeon makes an incision, approximately 2.5 to 3.0 mm long, where suitable to ablate the first tumor, and inserts ablation device 22 into the abdomen. Entry of ablation device 22 is observed using laparoscope 12. The surgeon uses imaging probe 24 to visualize the size and location of the tumors with respect to ablation device 22. Whenever possible, the placement and use of ablation device 22 is correlated with imaging probe 24 such that the electrode of ablation device 22 and the transducer of imaging probe 24 are substantially parallel to one another for the most effective placement of the ablation device 22. Imaging probe 24 may not be substantially parallel to ablation device 22 in all instances.

Next, at step 74, tenaculum 38 and imaging probe 24 are utilized to position and stabilize the uterus. In other embodiments, other uterine manipulators may be used to manipulate and stabilize the uterus. Attachment of a stabilization device which punctures or injures the serosal surface of the uterus is generally to be avoided. Advantageously, the position of the imaging probe 24, the ablation device 22, and the uterus are controlled without puncturing the uterus multiple times in accordance with the present invention.

At step 76, after the surgeon has stabilized the uterus and located the tumors, the surgeon guides ablation device 22 into a wall of the uterus. In one embodiment, the surgeon may press or tap against the uterus with the ablation device without penetration to verify position of the entry point with the imaging device. The surgeon may guide ablation device 22 by changing the position of the uterus relative to ablation device 22 as noted above. In addition, the surgeon may rotate the ablation device for better penetration of the uterine wall with less movement of the uterus. Rotation of the ablation device is also beneficial for penetration into and exiting from higher density tumors. Insertion of the ablation device may also be performed while applying energy to the needle to coagulate the track and to increase ease of insertion. Ablation device 22 has a plurality of markings (not shown) that enable the surgeon to note the depth of penetration of device 22. Confirmation of the location and placement of ablation device 22 are provided by laparoscope 12 and imaging probe 24. Imaging probe 24 is utilized in multiple planes (e.g., sagital and transverse) to confirm the position of the electrode associated with ablation device 22.

Next, at step 78, the surgeon advances the tip of ablation device 22 to an appropriate depth for treating a tumor. In doing so, the needle makes only a very small puncture. For example, an ablation device having a needle of 16 gauge may produce a puncture site of approximately 1 mm to 2 mm in diameter. The appropriate depth depends upon the size of the tumor and characteristics of the ablation device 22. The operator may elect to position the ablation device 22 in such a manner as to most effectively ablate the blood supply of the tumor based on findings from pre-operative as well as intra-operative imaging studies such as Doppler ultrasound. When ablation device 22 has been inserted to the appropriate depth, arms 26 of ablation device 22 are deployed to the appropriate extent in the tumor 28, as illustrated in FIG. 1. Visualization via the imaging probe 24 and the laparoscope 12 are used to ensure that all of the arms 26 remain within the confines of the tumor and do not extend outside of the organ. Arms 26 may effectively anchor ablation device 22 in tumor 28.

At step 80, the surgeon then records a baseline temperature of the tumor, usually 39-42 degrees Celsius. The temperature of the tumor is obtained by the thermocouples located at the distal ends of arms 26 of ablation device 22.

At step 82, the surgeon then ablates the tumor by supplying RF energy from generator 20 to ablation device 22. While generator 20 is activated, it is important to monitor the temperature or impedance at all parts of the ablation device. If the temperature or impedance at any part of ablation device 22 is abnormal, it could indicate that that part of the device is external to the organ.

RF energy is supplied to the tumor to raise the temperature of the tumor, such that it is in the range of between approximately 65° C. and 100° C., for about 14 minutes in one example. Cell death occurs at a temperature of about 65° C. However, a preferred target temperature range for ablating pelvic tumors is between 85° C. and 100° C. to promote conduction of heat throughout the ablation zone. For smaller tumors the target time may be between approximately 3 minutes and 10 minutes. One of ordinary skill in the art, however, will appreciate that ablation times of less than 3 minutes may also be adequate.

In one embodiment, a particularly dense tumor may be pre-heated to condition the tumor for ease of penetration and achievement of full deployment of the electrode resulting in maximal ablation volume. To pre-heat the tumor, the ablation device electrode may be deployed until significant resistance is encountered to further deployment. The generator is then activated and the tumor pre-heated to a temperature below the target temperature. Once the tumor and ablation arms 26 are heated, the ablation device is further deployed to a greater extent as desired. Multiple stages of heating may be required in extreme cases to achieve optimal deployment. In one example, if the deployment length desired is about 4 cm but the tumor is of a high density and deployment is difficult, the arms may be deployed to about 2 cm and the tumor area pre-heated to approximately 90 degrees Celsius to soften the fibroid and heat the arms 26. The arms may then be more easily and effectively further deployed in the heated fibroid to the desired length for full achievement of the ablation volume of the ablation device. Conventional ablation has disadvantageously deployed cold electrodes into an unheated target tumor for ablation.

The ablation device 22 may also be inserted into the tumor or organ while activated to facilitate placement into a particularly dense tumor or organ. In another embodiment, the electrode may be deployed in conjunction with withdrawal of the shaft to modify the shape of the ablation volume from spherical to ovular to advantageously ablate non-spherical shaped tumors.

The temperature of the tumor at various sites, as provided by the thermocouples, is monitored and recorded. Thus, at least a baseline starting temperature, half-time temperature, and end-of-ablation-period temperature are recorded for each ablation. While RF energy is being delivered to the tumor, the surgeon observes monitors 14 and 18 to ensure that none of the arms 26 of ablation device 22 extends beyond the tumor. The uterus may contract during ablation, causing arms 26 of ablation device 22 to project from the tumor and contact normal tissue, which may be damaged by the RF energy. When the tumor has been sufficiently ablated, energy from the energy source 20 is discontinued.

Periodically between ablations, as shown by step 84, the uterus is irrigated with fluid such as normal saline or Lactated Ringers. The fluid keeps the serosa moist and prevents drying as a result of the carbon dioxide gas that is infused into the abdomen during laparoscopy. Irrigation also removes blood, thereby inhibiting formation of fibrin which could trigger adhesion formation.

If the tumor is larger than the ablation capacity of the given ablation device, then at step 86, the surgeon may need to reposition ablation device 22 within another part of the tumor and reapply RF energy, repeating steps 76 through 84. Thus, if the tumors are greater in size than the ablation capacity of ablation device 22, or if suboptimal deployment or placement of the ablation device occurs, multiple ablations which may overlap may be necessary to ablate the bulk of the tumor. For tumors less than 5 cm, however, a single application of the RF energy is usually sufficient. Ablation devices are currently available which can potentially achieve a 7 cm ablation with a single application of energy.

The rate at which power is delivered to the ablation device 22 may be controlled to optimize ablation efficiency. Power may be delivered over time until a target temperature is reached in such a manner that charring or tissue dehydration proximate arms 26 is inhibited. Charring around the arms 26 is undesirable as it inhibits conduction of heat and may result in incomplete or irregular ablations. With small tumors, power may be delivered more quickly via manual power control, thus achieving target temperatures faster thereby decreasing overall operative time. Subserosal fibroids may also be treated without deployment of electrodes but with an active tip of the ablation device shaft, similar to a track ablation mode. Accordingly, three methods of ablation may be used, including but not limited to using an algorithm for the application of power to the ablation device, heating with manual power control of the energy generator, and destruction of tumors with no deployment of the electrode.

An intra-abdominal Doppler study may be performed after the ablation to confirm effective cessation of blood flow to the tumor. At least one Doppler transducer incorporated at the distal end of ablation device 22 or imaging probe 24 may be used to perform the Doppler analysis. In one embodiment, the ultrasound probe can transmit ultrasound for imaging as well as for Doppler analysis.

In a further embodiment, based upon the Doppler analysis, imaging probe 24 may then be used to occlude the uterine arteries by physical pressure against the arteries of interest where they insert into the uterus. Accordingly, blood flow through the uterus may be decreased, thereby reducing the cooling effect from blood circulation and thus more efficiently ablating the fibroid.

In yet another embodiment, once the arms of the ablation device are deployed and anchored in the fibroid, the uterus may be suspended or lifted by elevating the ablation device 22 to examine pelvic areas otherwise hidden from view.

At step 88, the surgeon then repositions ablation device 22 at the next tumor. The surgeon may leave ablation device 22 in the same track if the next tumor is along the same line of approach. The surgeon would retract arms 26, advance or withdraw ablation device 22 as needed, and then insert ablation device 22 into the next tumor. The surgeon would then repeat the ablation sequence of step 78 through step 86 described above.

If the subsequent tumor is in a different location, the surgeon may retract arms 26 of ablation device 22 and withdraw ablation device 22 from the uterus, while applying a mono-polar cautery to reduce or prevent bleeding from the ablation device track. Alternatively, rather than completely withdrawing ablation device 22 and re-inserting ablation device 22 at a new point of entry, repeating steps 72 through 86, the surgeon may withdraw ablation device 22 until it is only 0.5 cm to 1 cm deep within the uterus and adjust the uterus until the desired angle of approach is obtained. The ablation device 22 may then be inserted into the new tumor as previously described. Advantageously, imaging probe 24 and uterine manipulator 38 may be used to adjust the uterus.

In the case of multiple ablations, the ablation device may be removed entirely from the patient and cleaned with water and a soft brush to remove from the needle shaft and arms 26 adherent debris and tissue.

Small, superficial, subserosal fibroids (e.g., less than 1 cm) may be ablated using different techniques. In one example, a mono-polar cautery may be used at step 90. Bipolar paddles may also be used if the fibroid extends from the wall of the uterus. Similarly, if the tumor is pedunculated, the surgeon may treat and/or incise the stalk. Mono-polar or bipolar cautery may be applied to subserosal, intramural, and submucuos leiomyomata. In addition, other pelvic pathologies are treated as appropriate.

After all of the tumors have been ablated, at step 92, the surgeon confirms hemostasis, withdraws ablation device 22, and applies a mono-polar cautery with ablation device 22 to the puncture sites, if necessary. A small amount of irrigation fluid may be left in the pelvis.

Finally, at step 94, documentation, including videotapes, ultrasound photographs, and photographs from the laparoscope are obtained. The sleeves are opened to allow the escape of the carbon dioxide gas and a local anesthetic agent is injected into the skin incisions. The surgeon then repairs the fascia of the 10 mm incision using an absorbable suture and S-retractors to facilitate visualization. Alis™ clamps or other atraumatic clamps are used to grasp and elevate the fascial edges for suturing. The skin and subcutaneous tissue are closed in the standard fashion. The surgeon then removes the dispersive electrode 30 and the foley catheter and examines the surrounding skin.

The patient is transported to a recovery room, where she will remain until she is tolerating liquids, ambulating with assistance, and voiding adequately.

If the patient's uterus is very large (e.g., 16 weeks or greater), the above-described laparoscopic technique may be less effective. Accordingly, a direct trans-abdominal insertion of ablation device 22 may be performed with predominately laparoscopic confirmation (e.g., minimal intra-abdominal ultrasound confirmation). In this method the patient is prepared in the same manner as that described above at step 52. The surgeon also performs a pelvic examination, positions the patient, places a foley catheter and serial compression devices, arranges the equipment, makes an infra-umbilical incision, insufflates the patient's abdomen, and inserts laparoscope 12, as in step 54 through to step 62 above. Specifically, the surgeon inspects the abdomen and documents the presence or absence of bowel adhesions or other pathologic conditions that would render this method inappropriate without surgical correction. Lysis of abdominal adhesions may be performed as needed to establish normal anatomy. Radiofrequency ablation may then be performed as follows.

Next, the surgeon releases the $CO_2$ gas from the patient's abdomen, allowing the abdominal wall to contact an anterior portion of the uterus. A sterile cover drape over a transducer allows for trans-abdominal ultrasound imaging using a non-sterile transducer (not shown). The ultrasound is used to locate and measure the tumors.

The surgeon then makes an incision for ablation device 22 and inserts ablation device 22 percutaneously and trans-abdominally, using trans-abdominal ultrasonography to guide its insertion.

Ablation device 22 is positioned at a tumor and arms 26 are deployed in the tumor, just as described above with respect to the laparoscopic method. Prior to applying RF energy to the tumor, the surgeon insufflates the abdomen and performs a laparoscopy to confirm that none of the arms 26 of ablation device 22 extend beyond the uterine tissue.

The surgeon then applies RF energy to the tumor, in the same manner as described at step 80 through step 84 above, including recording the baseline, half-time, and end-of-ablation-period temperatures. The surgeon may use the same approach as described above to ablate multiple pelvic tumors. Upon withdrawal of the ablation device 22, the surgeon fulgurates the ablation device track with a mono-polar cautery under visualization through the laparoscope. Thus, remaining steps are the same as step 86 through step 94 described above.

The above-described methods enable the surgeon to ablate substantially all of a tumor from a single, ablation device puncture site but multiple punctures may be necessary for larger tumors. In addition, depending on the location of the tumors, multiple tumors may be ablated from a single puncture site. The methods further enable the surgeon to treat all sizes of tumors in any area of the pelvic and/or abdominal region.

The above-described embodiments of the present invention are merely meant to be illustrative and not limiting. Various changes and modifications may be made without departing from this invention in its broader aspects. For example, although the present invention has been described with respect to the treatment of uterine leiomyomata, the present invention may also be used to treat other pelvic tumors, such as those present in the ovaries. The present invention may be performed using a trans-cervical, a hysteroscopic, or a trans-vaginal technique, in addition to the laparoscopic and trans-abdominal techniques described above. Therefore, the appended claims encompass all such changes and modifications as falling within the true spirit and scope of this invention.

I claim:

1. A method of treating a tumor, comprising:
   inserting an ablation device into a pelvic region, the ablation device comprising an electrode, said electrode being contained within the ablation device;
   deploying a portion of the electrode from within the ablation device into a tumor;
   delivering a first dose of energy through the deployed portion of the electrode to pre-heat a portion of the tumor;
   deploying a larger portion of the electrode within the tumor after said delivering a first dose of energy; and
   delivering a second dose of energy after said deploying a larger portion of the electrode within the tumor through the electrode to ablate the tumor.

2. The method of claim 1, wherein the first dose of energy heats a portion of the tumor to a temperature under 100 degrees Celsius.

3. The method of claim 1, wherein the second dose of energy heats the tumor to a higher temperature than the first amount of energy.

4. The method of claim 1 further comprising insufflating the abdominal cavity.

5. A method as in claim 1, further comprising insufflating the abdomen to create an air pocket adjacent to the pelvic region and introducing an optical imaging device into said air pocket, said optical imaging device imaging the pelvic region.

6. A method as in claim 5, wherein said optical imaging device is positioned to image the uterus and said pelvic region is a uterus and an ultrasound probe is positioned against the uterus.

7. The method of claim 6, wherein the imaging probe is used to manipulate the position of the uterus relative to the electrode.

8. The method of claim 6, further comprising rotating the ablation device during insertion to reduce movement of the uterus.

9. The method of claim 6, wherein the ablation device includes a plurality of deployable arms and further comprising deploying the plurality of arms completely within the pelvic tumor.

10. The method of claim 6, wherein the imaging probe images an intra-abdominal region using ultrasound.

11. The method of claim 6, further comprising positioning the ablation device with a laparoscope.

12. The method of claim 6, further comprising removing the ablation device from the pelvic region, while cauterizing a track of the ablation device.

13. The method of claim 6, further comprising performing an intra-abdominal Doppler analysis of the pelvic area.

14. A method as in claim 6, further comprising imaging said ablation device.

15. The method of claim 5, wherein inserting the ablation device comprises inserting the ablation device into a fibroid in a uterus.

16. The method of claim 5, wherein inserting the ablation device comprises inserting through an abdomen and into the uterus.

17. The method of claim 5, wherein inserting the ablation device comprises inserting through a cervix and into the uterus.

18. The method of claim 5, wherein the pelvic region is the uterus and further comprising repositioning the uterus relative to the ablation device.

19. The method of claim 1, further comprising inserting an ultrasound probe into an incision proximate a top of a uterus.

20. The method of claim 5, wherein delivering energy includes delivering RF energy to the pelvic tumor.

21. The method of claim 1, further comprising:
repositioning the ablation device within a second pelvic tumor;
positioning the electrode within the second pelvic tumor using an imaging probe separate from the ablation device; and delivering energy through the electrode to directly ablate the second pelvic tumor.

22. The method of claim 21, wherein the second to be ablated pelvic tumor is located closer to a vasculature than a first ablated pelvic tumor.

23. The method of claim 1, further comprising occluding an artery entering the uterus.

24. A method as in claim 1, wherein the pelvic region is a uterus and the tumor is a uterine fibroid, and further comprising positioning an ultrasound probe adjacent or in the uterus.

25. A method as in claim 24, further comprising occluding an artery entering the uterus by applying pressure to said artery.

26. A method as in claim 25 further comprising repositioning the uterus.

27. A method as in claim 25, further comprising imaging the uterine fibroid with a laparoscope and wherein the abdominal cavity is inflated using the insufflation apparatus to create an air pocket which extends from said laparoscope to the uterus.

28. A method as in claim 1 wherein the pelvic region is a uterus and further comprising repositioning the uterus.

29. A method of treating a pelvic tumor comprising:
inserting an ablation device into a tumor in a pelvic region, wherein the ablation device includes at least one electrode;
advancing a first portion of the electrode from the ablation device;
applying energy while said first portion is in contact with the tumor for a first period of time, said first period of time being sufficient to soften said tumor;
advancing a further portion of the electrode from the ablation device;
further applying energy to said electrode during a second period of time, said further portion being deployed in said tumor during said second period of time imaging the at least one electrode within a pelvic tumor with a laparoscope; and
imaging the ablation device with an intra-abdominal imaging probe separate from the ablation device.

30. The method of claim 29, wherein the imaging probe is an intra-abdominal ultrasound probe.

31. The method of claim 29, wherein the pelvic tumor is a uterine fibroid.

32. The method of claim 29, wherein the ablation device includes a plurality of deployable electrode arms.

33. The method of claim 32, wherein the delivered energy is RF energy.

34. The method of claim 33, further comprising repeated advancements of the plurality of electrode arms, each successive advancement followed by a respective successive application of energy for successive periods of time sufficient to soften successive portions of the pelvic tumor.

35. The method of claim 34, wherein said successive portions of said successive advancements are distinct separate movements of said electrode arms said movements occurring during periods of time which are separated by periods of non-movement of said electrode arms, and said movements being advancements of said electrode arms exposing a greater portion of a respective electrode arm.

36. The method of claim 29, further comprising manipulating the pelvic region with the intra-abdominal imaging probe to position and stabilize the pelvic region.

37. A method as in claim 29, wherein an insufflation device is used to create an air space adjacent the uterine fibroid.

* * * * *